United States Patent [19]

Liebl et al.

[11] Patent Number: 5,304,142
[45] Date of Patent: Apr. 19, 1994

[54] DILATOR - INTRODUCER LOCKING HUB AND SHEATH VALVE APPARATUS

[75] Inventors: David A. Liebl, Saint Louis Park; Bruce L. Funk, Maplewood, both of Minn.

[73] Assignee: Medamicus, Inc., Minneapolis, Minn.

[21] Appl. No.: 925,092

[22] Filed: Aug. 4, 1992

[51] Int. Cl.[5] .............................................. A61M 29/00
[52] U.S. Cl. ................................. 604/167; 604/169; 606/191
[58] Field of Search ...................... 606/185, 191, 198; 604/167, 169, 164

[56] References Cited

U.S. PATENT DOCUMENTS

| 4,935,010 | 6/1990 | Cox et al. ............................ 604/167 |
| 5,186,712 | 2/1993 | Kelso et al. .......................... 604/164 |
| 5,190,050 | 3/1993 | Nitzsche .............................. 604/164 |

FOREIGN PATENT DOCUMENTS 3444232  6/1986  Fed. Rep. of Germany ...... 606/191

*Primary Examiner*—Tamara L. Graysay
*Attorney, Agent, or Firm*—Clayton R. Johnson

[57] ABSTRACT

A dilator is axially movable to have its tubular member movably extended through the tubular portion of an introducer with the dilator hub abuttable against the tubular portion proximal edge. A locking finger mounted to the introducer tab (or handle) is radially extendable into a hub recess to lockingly retain the dilator and introducer in a coupled relationship to prevent accidental axial separation. The recess is formed by the hub main body and a radially extending flange to open radially outwardly. In one embodiment, the introducer tab is of a flexibility for being manually bent to move the locking finger out of the recess to permit axial separation while in a second embodiment, a flange notch is provided for the locking finger to relatively move axially therethrough when the dilator and introducer are relatively rotated from a position where the locking finger abuts against the flange. In the third embodiment, a slider is axially movable on the tab between a locking finger locked coupling position, a valving position blocking fluid flow through the tubular portion when the dilator and introducer are axially separated, and a valve open position permitting axial separation of the dilator and the introducer; while a fourth embodiment has a slider and an introducer notched flange.

18 Claims, 3 Drawing Sheets

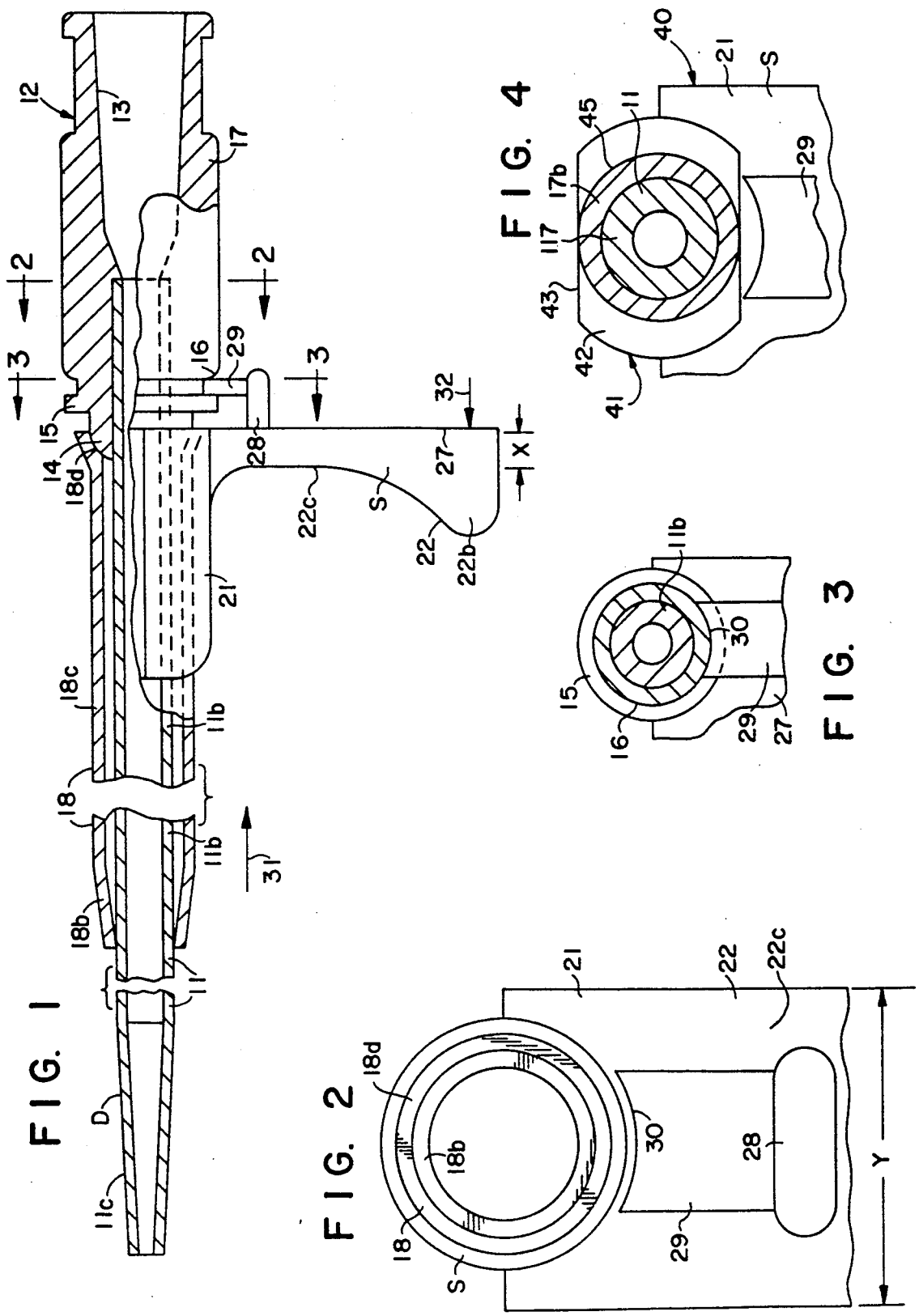

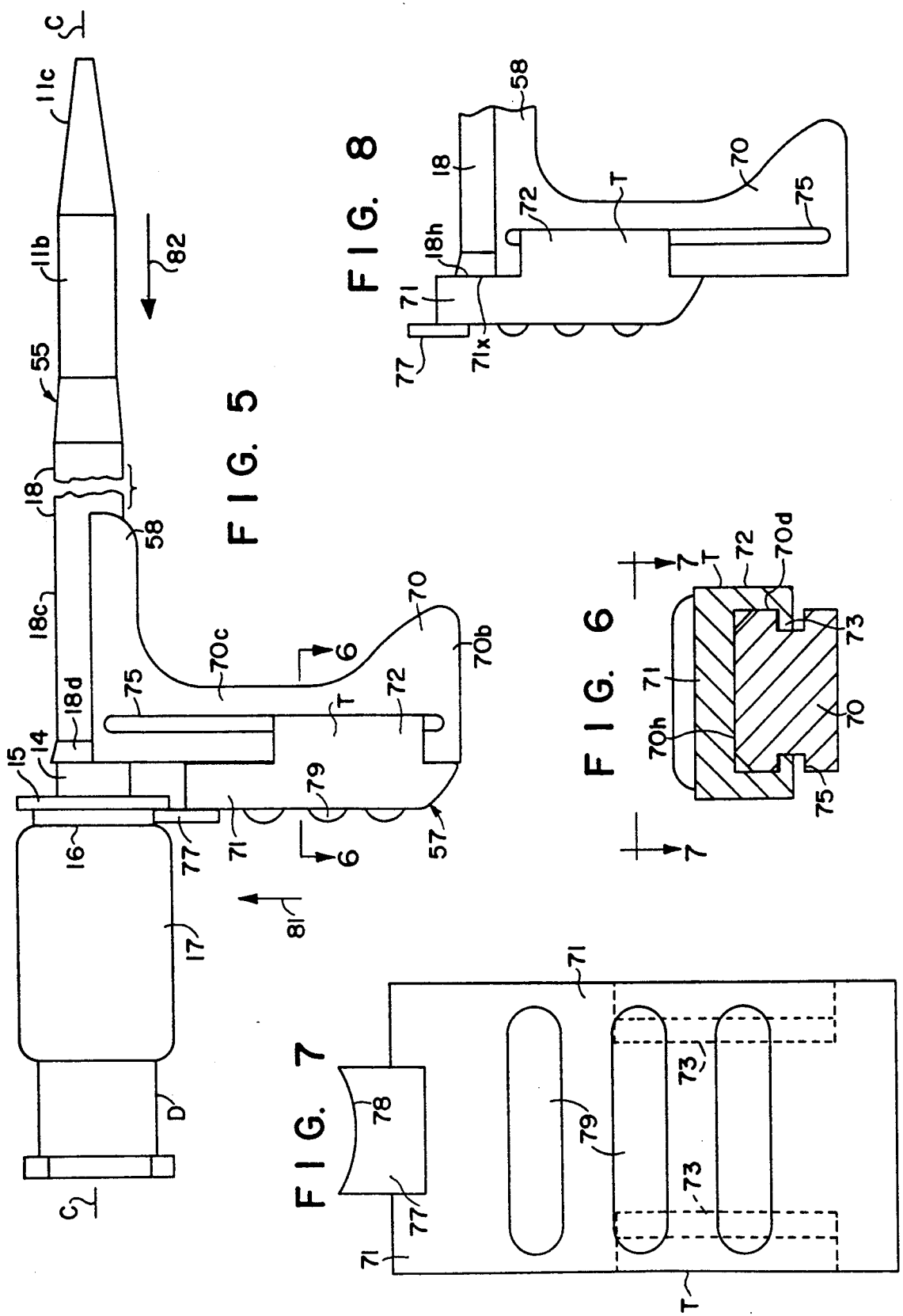

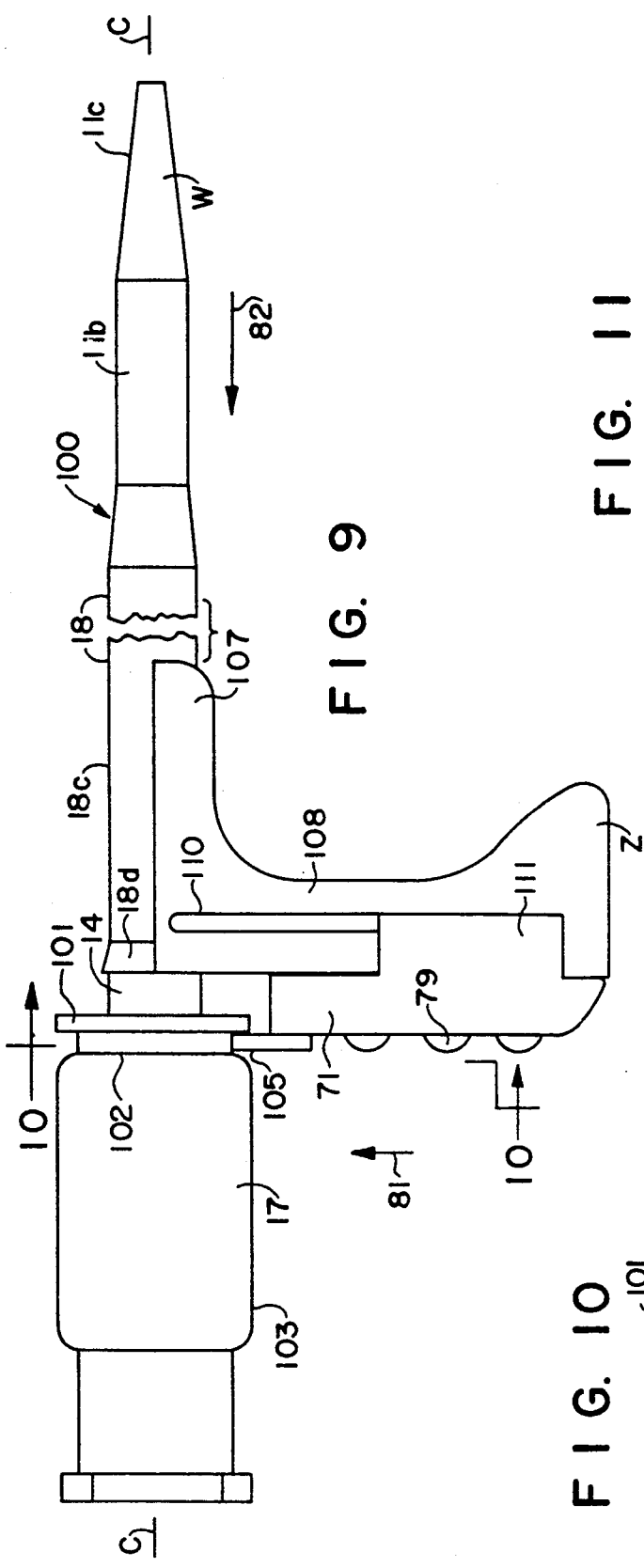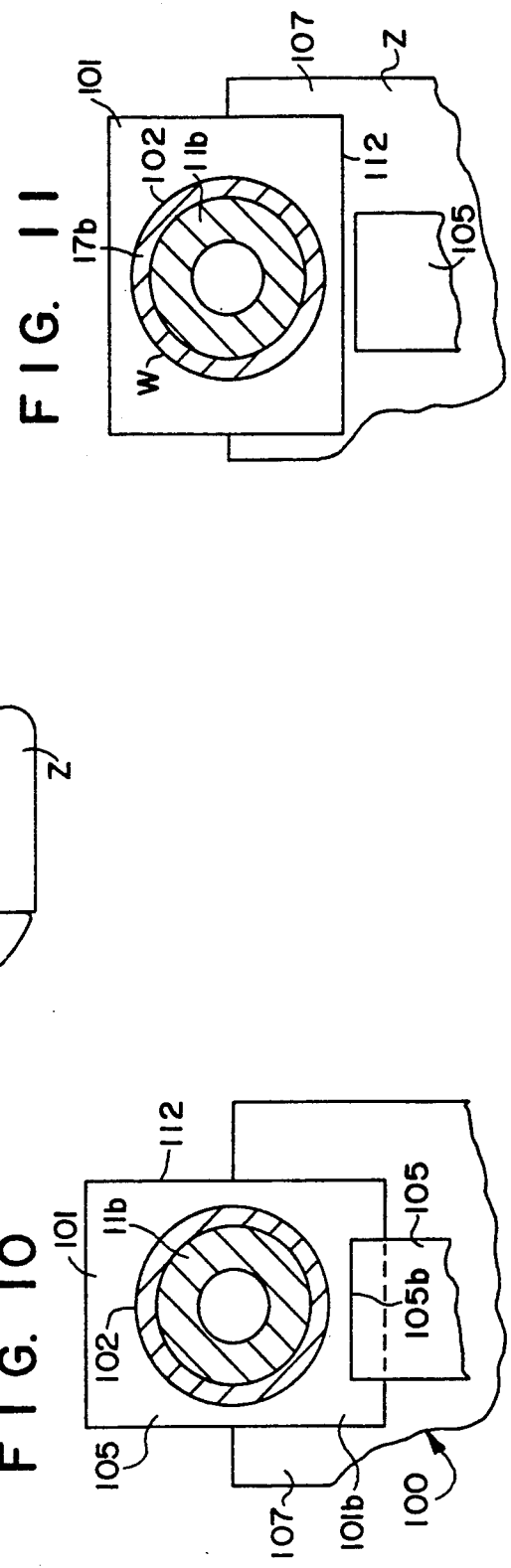

1

DILATOR - INTRODUCER LOCKING HUB AND SHEATH VALVE APPARATUS

BACKGROUND OF THE INVENTION

This invention relates to a dilator and an introducer having cooperating parts for releasably locking the dilator and introducer together with the dilator extending into the introducer and axially therethrough.

In the prior art it is known to provide dilator and introducer tubular portions with interference fits in an attempt to prevent the dilator from accidentally separating from the introducer and falling onto a surface whereby the dilator becomes contaminated and has to be thrown away. Further, it is known to provide an introducer with radially outwardly extending, diametric opposite tabs at its proximal end and a dilator having a hub portion that has diametric opposite, axially extending clip legs with leg axial mid-portion joined to the hub, axial inner hook ends for abutting against the axial inner (distal) surfaces of the tabs of the introducer and axial outer portion that when manually squeezed together (toward the hub), move the hook ends apart to permit axial separation of the dilator from the introducer. This results in the dilator hub end portion being somewhat more bulky than desired.

Additionally, problems are encountered when a dilator introducer combination extends within a living body, for example a subclavian vein, and only the dilator is removed. With presently known introducers, in order to prevent either the loss of blood from the human body or air being aspirated into the body, through the introducer, the doctor or another party places their thumb over the introducer proximal end.

In order to overcome problems such as described above and to provide an improved structural arrangement for releasably retaining a dilator and introducer in a coupled relationship, as well as achieving other advantages, this invention has been made.

A mechanical locking member is provided on the tab of an introducer to removably remain in an annular groove, or a radially recessed arcuate portion, of the hub of a dilator to lockingly retain the dilator to the introducer with the tubular member of the dilator extending into the tubular portion of the introducer. In one embodiment, the locking finger is resiliently retained in the groove while in another embodiment, a hub flange is rotatable relative to the introducer locking finger between a position permitting axial separation of the dilator from the introducer and a position blocking the axial separation of the dilator from the introducer. In a third embodiment, a slider is mounted on the introducer tab, the tab in turn mounting the locking finger for movement between a dilator introducer coupling position and a dilator introducer uncoupling position, the slider also serving to substantially eliminate egress flow through the introducer when the dilator has been removed from the introducer.

One of the objects of this invention is to provide a new and novel introducer and dilator combination that is releasably couplingly engageable for retaining the dilator tubular portion extending within the introducer tubular portion. Another object of the invention is to provide new and novel means on an introducer to lockingly couple to a conventional hub of a catheter or dilator to prevent accidental separation. An additional object of this invention is to provide an introducer having new and novel means for selectively blocking fluid flow through the introducer tubular member when the dilator has been axially separated from the introducer.

BRIEF DESCRIPTION OF THE DRAWINGS

FIG. 1 is in part an axial cross sectional view and in part a side view of the first embodiment of the dilator and introducer of the invention with axial intermediate portions broken away and the locking finger of the introducer being extended into the annular groove of the dilator hub, said view showing the dilator and introducer in a coupled condition;

FIG. 2 is a fragmentary transverse cross sectional view of the introducer that is generally taken along the line and in the direction of the arrows 2—2 of FIG. 1 with the dilator removed;

FIG. 3 is a fragmentary transverse cross sectional view of the structure of FIG. 1 that is generally taken along the line and in the direction of the arrows 3—3 of FIG. 1;

FIG. 4 is a view that generally corresponds to FIG. 3, other than it is of the second embodiment and the dilator is shown in an unlocked condition;

FIG. 5 is a side view of the third embodiment of the introducer and dilator of this invention with an axial intermediate part broken away and the locking finger of the introducer extended into the hub groove of the dilator in the dilator introducer locked coupling position;

FIG. 6 is an axial cross sectional view that is generally taken along the line and in the direction of the arrows 6—6 of FIG. 5;

FIG. 7 is a transverse view of the slider of the third embodiment that is generally taken along the line and in the direction of the arrows 7—7 of FIG. 6;

FIG. 8 is a fragmentary side view of introducer showing the slider in its valve closed position with the dilator removed:

FIG. 9 is a view that corresponds to FIG. 5 other than it is of the fourth embodiment;

FIG. 10 a fragmentary cross sectional view that is generally taken along the line and in the direction of the arrows 10—10 of FIG. 9; and FIG. 11 is the same as FIG. 10 other than the dilator has been rotated relative to the introducer to a position for being axially removed from the introducer.

Referring in particular to FIGS. 1-3, the first embodiment of the invention includes an axially elongated dilator D having a central axis C—C and a hub (dilator fitting or connector), generally designated 12, and a tubular member 11 together with an introducer (sheath) S having a tab mount 21 and a radially elongated tab joined thereto. The dilator D is conventional and has a bore 13 extending axially through the hub. The constant diameter tubular part 11b of the tubular member 11 has a circumferential outer peripheral surface and an axial distal end portion tat extends into the distal portion of the bore 13 and is joined to the adjacent part of the hub. The tubular member 11 also has a distal end 11c that has a radial outer, conical surface that is of progressively reduced diameters in a distal direction relative to the hub. The hub has an annular flange 15 that is of a larger diameter than the distal end portion 14 and is proximally adjacent thereto. The flange and the main body 17 of the hub provide an annular groove (locking finger recess) 16 that opens radially outwardly relative to the central axis C—C, the groove being axially much more closely adjacent to the hub distal end than the proximal end.

The introducer S includes an axially elongated tubular portion 18 having a frustoconical, proximal part 18d to form a close fit with an outer peripheral part of the hub distal end portion 14, while the proximal part of the generally constant diameter, axial intermediate part 18c of the tubular portion 18 is joined to the minor base of part 18d. The axial opposite end of the part 18c is joined to the major base of the frustoconical tubular part 18b, the minimum diameter of part 18b being such that the constant diameter part 11b of the dilator may be extended therethrough. The tubular member 11 is of an axial length to extend more distally remote from the hub, when the hub is in abutting relationship to part 18d, than the frustoconical part 18b.

The introducer includes a tab mount 21, which is axially elongated, joined to an outer peripheral part of the proximal end portion of the axially elongated tubular portion 18 while a radial elongated tab 22 extends radially outwardly of the proximal part of the tab mount and is joined thereto. The combination of the tab mount and the tab have a transverse proximal end surface portion 27. A lock member includes an axially extending leg 28 secured to surface portion 27 and a radially extending locking finger 29 that has one end joined to the leg 28 in axial spaced relationship to the surface 27 and an opposite (radial inner) end that includes an edge 30 which may be arcuately curved about the central axis C—C. The locking finger is transversely spaced from surface 27 by a distance sufficient to be in transverse (radial) alignment with the groove 16 when hub portion 14 is in abutting relationship to introducer part 18d, while the locking finger is of a transverse (radial) dimension to extend into groove 16 when portions 14 and 18d are in abutting relationship for retaining the introducer and dilator in a locked coupled relationship. It is to be understood that edge 30 may be linear, concave or other shapes as long the locking finger in its FIG. 3 position will retain the dilator and introducer in their locking coupled position.

The minimum axial dimension X of the tab radial intermediate portion 22c in a direction perpendicular to surface 27 is substantially less than the corresponding dimension of the tab end portion 22b that is radially remote from the tab mount. Further, the dimension Y of the tab which is taken at right angles to the radial dimension of the tab and dimension X is substantially greater than dimension X, advantageously at least twice as great. The tab is made of a plastic, is of dimensions, and is sufficiently rigid that it will retain its shape such as shown in FIG. 1 until manually forced to flex relative to the tab mount and/or the introducer tubular portion 18. However, in view of the above relative dimensions and the flexibility of the tab, the tab may be sufficiently bent relative to the tab mount to move the locking finger out of the groove (from the position shown in FIG. 1) to be radially entirely out of axial alignment with the flange 15. That is, the tab, leg 28 and the locking finger are of sufficient rigidity that when the locking finger extends into the groove 16, the locking finger will prevent the dilator from accidentally moving in the axial direction of the arrow 31 relative to the introducer; and the relative axial dimensions of the locking finger and the groove 16 are such that the hub distal end portion is either retained in abutting relationship to tubular part 18d or axially very closely adjacent thereto. During the time the dilator and introducer are couplingly engaged, the flange 15 extends radially to be axially between the locking finger 29 and at least one of the tab and the tab mount. Advantageously, the flange 15 has a circular outer peripheral surface whereby when the locking finger is extending into the groove (finger extends in axial alignment with the flange), the dilator and introducer remain in a locked coupled condition regardless of the angular relationship of the dilator relative to the introducer.

In the event it is desired to separate the dilator from the introducer, or extend the dilator into the introducer and move the dilator axially into locking engagement therewith, the remote end portion 22b of the tab is forced to move in a distal direction relative to the tab mount whereby the tab flexes (bends) about axes (a) radially intermediate the tubular portion 18c and the radial outer part of the tab; (b) distally of the surface 27; and (c) generally parallel to the surface 27, and perpendicular to an axial plane containing the central axis of the tubular portion 18, bisecting the tab and extending perpendicular to a plane that extends generally parallel to the surface 27. For example, with the dilator lockingly coupled to the introducer, the elongated tab 22 may be grasped between the thumb and index finger of one hand with the thumb against surface 27. The hub 12 may be pushed or grasped with the other hand and moved in a direction radially away relative to the locking finger to thus locate the locking finger entirely out of the groove. While the locking finger is out of the groove, the dilator may be axially separated from the introducer by moving the dilator in an axial direction opposite of arrow 31 while holding the introducer stationary.

Referring to FIG. 4, the second embodiment of the invention, generally designated 40, includes an introducer that is the same as that of the first embodiment, or may have a tab of a greater rigidity than that of the first embodiment, and a dilator, generally designated 41, that is the same as the first embodiment, other than for an annular flange 15. As shown, there are provided arcuate flanges 42 which are arcuately spaced to provide notches 43, and are of radial dimensions to extend between the locking finger and the tab i.e. when the dilator is angularly rotated relative to the introducer from the FIG. 4 position. The flanges 42, in conjunction with the hub main body portion of hub 117 provide arcuate groove portions (locking finger recesses) 45 that open radially outwardly relative to the central axis of the dilator. The arcuate dimension of each notch 45 is sufficiently greater than the corresponding dimension of the transverse adjacent part of the locking finger whereby the dilator can be rotated to the position of FIG. 4 and then the dilator can be moved axially away from the introducer without a flange portion 42 abutting against finger 29. Accordingly, with the second embodiment, it is not necessary to make the tab of a flexibility such as described relative to the first embodiment since by merely rotating the dilator relative to the introducer, the dilator and introducer can be relatively moved between a locking coupled condition wherein the finger 29 extends into the groove in axial alignment with one of the flanges, and an unlocked separated (uncoupled) condition wherein the finger 29 is out of axial alignment with the flanges 42. There can be provided only a single notch, or, depending upon the relative arcuate dimensions of the notches and the radial inner portion of the finger, two or more notches may be provided. Even though the combination of the two flanges 42 do not extend circumferentially around the hub portion 17b of hub 117, it is to be understood that an annular flange may be provided with one or more notches that open radially outwardly to have the locking finger relatively moved axially therethrough, but not extend radially inwardly to the hub portion 17b. This assumes that the dilator and introducer may be relatively moved, including rotating, between locked coupled, and unlocked uncoupled, positions.

Referring to FIGS. 5-8, the third embodiment of the invention, generally designated 55, includes a dilator D that may be the same as that of the first embodiment, and an introducer, generally designated 57. The tubular portion 18 and the tab mounting portion 58 of the introducer 57 may be the same as the corresponding parts of the first embodiment. However, the tab 70 of the third embodiment differs from that of the first embodiment. The radially elongated tab 70 extends generally radially outwardly of the tab mount 58 and has a radial intermediate portion 70c and a radial remote end portion 70b. The tab has generally radially extending, substantially parallel sides 70d and a proximal surface 70h extending between the sides that advantageously is nearly planar.

A combination valve and locking finger slider T is mounted on the tab for radial movement relative to the tubular portion 18. The slider has a web portion 71 that extends generally parallel to surface 70h in closely adjacent relationship thereto, opposed legs 72 extending along sides 70d of the tab and joined to the web, and inturned portions 73 joined to the legs remote from the web and extending into the radially elongated, parallel grooves 75. The distal, radially extending surface of the web may be planar throughout its radial length or may have a radial inner, distal surface portion that is of a slight partially spherical shape to form a better fluid closure with the proximal terminal peripheral edge 18h of the frustoconical part 18d when the slider is in its valve closed position of FIG. 8. Ribs 79 are joined to web 71 to facilitate moving the slider relative to the tab in the radial direction of arrow 81 and the radial opposite direction. A radially extending locking finger 77 has a radial outer end portion fixedly secured to the web 71 whereby the finger radial inner end portion extends radially inwardly toward the central axis C—C to be more closely adjacent to the central axis than the web when the slider is in its dilator and introducer locked coupling position shown in FIG. 5. The finger is of an axial thickness to be extendable into the hub annular groove 16. The radial inner end of the finger has an edge 78 that may be arcuately curved about the central axis C—C.

The grooves 75 are substantially longer than the inturned portions 73 and extend generally radially in the tab to open outwardly through the tab side walls 70d. The relative radial lengths of the grooves 75 and legs 72 may be such that the slider is movable in a direction opposite of arrow 81 from that shown in FIG. 5 to move the radial inner terminal edge 78 of the locking finger out of the groove 16 to permit the dilator being axially moved in the direction of arrow 82 to completely separate from the introducer. Further, the relative lengths of the slots and the slider legs are such that the slider is radially movable relative to the tab to the position shown in FIG. 8 wherein the distal surface of the web 71 abuts against the free transverse peripheral edge (proximal edge) 18h of frustoconical part 18d to block fluid flow in the direction of the arrow 82 outwardly through the introducer tubular portion, or alternately, in the opposite direction into the introducer tubular portion. Accordingly, for example, the introducer can have its distal end left in a body vessel and after the dilator is withdrawn from the introducer, the slider can be moved in the direction of the arrow 81 to the FIG. 5 position to prevent egress of body fluid or ingress of air through the introducer.

The slider forms a sufficiently close frictional fit with the tab 70 so as to remain in the position relative to the tab to which it has been manually moved. Thus, the slider is manually movable from a position below that shown in FIG. 5 (slider uncoupled, valve open position) to permit the dilator being moved to have its tubular member extended into the introducer tubular portion and the groove 16 radially aligned with the locking finger, the hub distal portion 14 in abutting relationship with the frustoconical part 18d limiting the movement of the dilator in the direction opposite arrow 82. After the dilator has been moved axially to have the groove 16 radially aligned with the locking finger, the slider is moved from its slider uncoupled, valve open position to its dilator-introducer coupled position of FIG. 5.

Referring to FIGS. 9-11, the fourth embodiment of the invention, generally designated 100, includes an introducer Z, and a dilator which may be the same as that of the second embodiment. However, as shown, the dilator W of the fourth embodiment may differ from the dilator of the second embodiment in that the dilator W has a generally rectangular flange 101 in combination with the hub main body 103 form recessed grooved portions 102 such as shown in FIG. 10. The elongated edges of the flange provide cut outs or notches 112.

The introducer Z may be the same as that of the third embodiment other than for the radial length of the tab grooves, and if desired, the radial inner end portion of the locking finger. As shown in FIG. 10, the locking finger 105 of the fourth embodiment has a radially inner, generally linear terminal edge 105b, the slider 111 of the fourth embodiment being the same as that of the third embodiment and mounts the locking finger in the same manner.

The tab mount 107 is joined to the introducer tubular portion 18 and mounts the tab 108 to extend radially outwardly thereof. The slider grooves 110 in the tab 108 are of radial lengths that the slider is radially movable from the valve closed position (not shown), which corresponds to the FIG. 8 position of the third embodiment, to the slider dilator introducer locking coupled position of FIG. 10. That is, when the slider is in its valve closed position, its radial inner, distal surface portion abuts against the proximal terminal edge portion of the introducer tubular portion to block fluid flow through the introducer tubular portion. When the slider is in the introducer locking coupled position and the dilator is in its FIG. 10 lockingly coupled position, one flange portion (arcuate portion) 101b is located axially between the locking finger 105 and at least one of the tab mount and the tab. However, upon rotating the dilator relative to the introducer until a flange potion is no longer axially between the locking finger 105 and at least one of the tab and the tab mount (unlocked position), the dilator may be freely axially separated from the introducer (without having to move the locking finger relative to the central axis C—C). The grooves 110 are not of a length that the slider may be radially moved sufficiently remote from the central axis that the dilator may be freely axially separated from the introducer. That is the slider 111 can not be moved more remote from the central axis C—C than that shown in FIG. 10.

The flange, notches and the finger radial inner end of each of the second and the fourth embodiment may be of varying shapes as view in a transverse plane as long as their relative transverse sizes and shapes are such that the finger in one angular position relative to the flange, the dilator may not be freely axially separated from the introducer; and in a second angular position the dilator may be freely axially separated from the introducer as is also applicable to the second embodiment. Additionally the flange and the locking finger radial inner end of each of the first and third embodiments may be of varying shapes as long as these members function in the manner described.

As may be seen from each of FIGS. 1, 5 and 9, the locking finger is located to be axially proximally of the proximal terminal edge of the proximal frustoconical end portion of the introducer and the respective tab and thus is axially proximal of the tubular portion 18 of the introducer.

What is claimed is:

1. An introducer dilator combination comprising a dilator having an axially elongated dilator member that has a proximal end portion and a generally circular outer peripheral surface, and a hub having an axial distal end portion joined to the proximal end portion of the dilator member and proximal end portion; and an introducer that includes an axially elongated tubular portion for having the dilator member extending thereinto, said tubular portion having a proximal end portion, and tab means joined to the proximal end portion of the tubular portion to extend radially outwardly therefrom for facilitating manual control of the movement of the tubular portion, the dilator and introducer having cooperating means for releasably retaining the dilator and introducer in a coupled relationship with the dilator member extending within the tubular portion, the cooperating means including locking finger means mounted to the tab means and a hub flange that at least in part defines a radially outwardly opening grooved portion, the locking finger means and the hub flange being relatively movable between a dilator and introducer locked coupling position that the locking finger means and the hub flange are in axial alignment with one another whereby the dilator is lockingly retained in a substantially axially fixed position relative to the introducer, and a dilator and introducer unlocked uncoupling position that the locking finger means and the hub flange are out of axial alignment with one another whereby the dilator may be axially separated from the introducer, the proximal end portion of the tubular portion having a proximal terminal edge and the locking finger means having a locking finger movable into said grooved portion and means mounted to the tab means for mounting the locking finger axially proximally of the proximal terminal edge.

2. The combination of claim 1, further characterized in that the axially elongated dilator member comprises an axially elongated tubular member, that the hub has a bore extending axially therethrough that opens to the tubular member, that the tab means comprises a tab extending generally radially outwardly of the tubular portion and that the means mounted to the tab means comprises means for mounting the locking finger proximally of the tab.

3. An introducer dilator combination comprising a dilator having an axially elongated dilator member that has a proximal end portion and a generally circular outer peripheral surface, and a hub having an axial distal end portion joined to the proximal end portion of the dilator member and a proximal end portion; and an introducer that includes an axially elongated tubular portion for having the dilator member extended thereinto, said tubular portion having a proximal end portion, tab means joined to the proximal end portion of the tubular portion to extend radially outwardly therefrom for facilitating manual control of the movement of the tubular portion, the proximal end portion of the introducer tubular portion having a proximal terminal peripheral edge, the tab means including a tab extending generally radially relative to the tubular portions, and means for joining the tab to the tubular portion proximal end portion, the dilator and introducer having cooperating means for releasably retaining the dilator and introducer in a coupled relationship with the dilator member extending within the tubular portion, the cooperating means including locking finger means mounted to the tab means and a hub flange that at least in part defines a radially outwardly opening grooved portion, the locking finger means and the hub flange being relatively movable between a dilator and introducer locked coupling position that the locking finger means and the hub flange are in axial alignment with one another whereby the dilator is lockingly retained in a substantially axially fixed position relative to the introducer, and a dilator and introducer unlocked uncoupling position that the locking finger means and the hub flange are out of axial alignment with one another whereby the dilator may be axially separated from the introducer, the locking finger means including a generally radially extending locking finger having a radial inner end portion of a slider mounting the locking finger for movement therewith, the slider having a radial inner, distal surface portion for abutting against said peripheral edge to substantially block fluid flow through the tubular portion when the dilator member is axially separated from the tubular portion, and the slider being mounted on the tab for limited slidable movement between a first limit position wherein the distal surface portion substantially blocks fluid flow through the tubular portion when the dilator is axially separated from the introducer, and a second limit position furthest remote from the first position that said surface portion is radially spaced from said peripheral edge, the hub flange having a notch means of a circumferential dimension that is greater than a corresponding circumferential dimension of the finger radial inner end portion for having the finger radial inner end portion move axially therethrough when the slider is in its second position, the dilator being angularly movable relative to the introducer between a first angular position that the finger is abuttable against the hub flange to block axial separation of the dilator from the introducer when the dilator member extends within the tubular portion and a second angular position that the finger radial inner end portion is axially aligned with the notch means to permit free axial separation of the dilator from the introducer when the dilator is extended into the introducer.

4. An introducer dilator combination comprising a dilator having an axially elongated dilator member that has a proximal end portion and a generally circular outer peripheral surface, and a hub having an axial distal end portion joined to the proximal end portion of the dilator member and a proximal end portion; and an introducer that includes an axially elongated tubular portion for having the dilator member extended thereinto, said tubular portion having a central axis and a proximal end portion, and tab means joined to the proximal end portion of the tubular portion to extend radially outwardly therefrom for facilitating manual control of the movement of the tubular portion, the tab means including a tab extending generally radially relative to the tubular portion and means for joining the tab to the tubular portion proximal end portion, the dilator and introducer having cooperating means for releasably retaining the dilator and introducer in a coupled relationship with the dilator member extending within the tubular portion, the cooperating means including locking finger means mounted to the tab means and a hub flange that at least in part defines a radially outwardly opening grooved portion, the locking finger means and the hub flange being relatively movable between a dilator and introducer locked coupling position that the locking finger means and the hub flange are in axial alignment with one another whereby the dilator is lockingly retained in a substantially axially fixed position relative to the introducer, and a dilator and introducer unlocked uncoupling position that the locking finger means and the hub flange are out of axial alignment with one another whereby the dilator may be axially separated from the introducer, the locking finger means including a generally radially extending locking finger and means mounted to the tab for moving the finger out of axial alignment with the hub flange to permit axial separation of the dilator from the introducer.

5. The combination of claim 4, further characterized in that the finger has a radial inner end portion for abutting against the hub flange, and that the hub flange has a notch means of a circumferential dimension that is greater than a corresponding circumferential dimension of the finger radial inner end portion for having the finger radial inner end portion moving axially therethrough, said notch means being one of circumferentially aligned with the finger and axially more closely adjacent to the tubular portion than the finger.

6. The combination of claim 4, further characterized in that the tab has a remote end portion that is radially remote from the tubular portion, and that the means for joining the locking finger to the tab comprises a leg joined to the tab to extend proximally relative thereto for mounting the locking finger, the tab, the leg and the finger being of a flexibility such that upon bending the tab remote end portion, thereby moving the finger member relative to the hub flange from the dilator and introducer locked coupling position to the dilator and introducer unlocked uncoupling position.

7. The combination of claim 6, further characterized in that the hub flange is annular and that the tab remote end portion is substantially radially more remote from the tubular portion than said leg.

8. An introducer dilator combination comprising a dilator having an axially elongated dilator member that has a proximal end portion and a generally circular outer peripheral surface, and a hub having an axial distal end portion joined to the proximal end portion of the dilator member and a proximal end portion; and an introducer that includes an axially elongated tubular portion for having the dilator member extended thereinto, said tubular portion having a central axis, and tab means joined to the proximal end portion of the tubular portion to extend radially outwardly therefrom for facilitating manual control of the movement of the tubular portion, the tab means including a tab extending generally radially relative to the tubular portion and means for joining the tab to the tubular portion proximal end portion, the dilator and introducer having cooperating means for releasably retaining the dilator and introducer in a coupled relationship with the dilator member extending within the tubular portion, the cooperating means including locking finger means mounted to the tab means and a hub flange that at least in part defines a radially outwardly opening grooved portion, the locking finger means and the hub flange being relatively movable between a dilator and introducer locked coupling position that the locking finger means and the hub flange are in axial alignment with one another whereby the dilator is lockingly retained in a substantially axially fixed position relative to the introducer, and a dilator and introducer unlocked uncoupling position that the locking finger means and the hub flange are out of axial alignment with one another whereby the dilator may be axially separated from the introducer, the locking finger means including a generally radially extending locking finger and a slider means for moving the finger out of axial alignment with the hub flange to permit axial separation of the dilator from the introducer and alternately into axial alignment with the hub flange, said slider means being mounted to the tab for slidable movement relative thereto.

9. The combination of claim 8, further characterized in that the tubular portion has a proximal, free terminal peripheral edge, that the slider means is mounted on the tab for slidable movement between the dilator and introducer locked coupling position in which the finger is radially spaced from the central axis, and the dilator and introducer unlocked uncoupling position radially spacing the finger further from the central axis than when the slider means is in the dilator and introducer locked coupling position.

10. The combination of claim 8, further characterized in that the proximal end portion of the introducer tubular portion has a proximal terminal peripheral edge, that the slider means has a radial inner, distal surface portion for abutting against said peripheral edge to substantially block fluid flow through the tubular portion, and that the slider means is mounted on the tab for slidable movement between the dilator and introducer unlocked uncoupling position wherein said surface portion is radially spaced from said peripheral edge and a position wherein the distal surface portion substantially blocks fluid flow through the tubular portion.

11. An introducer dilator combination having a central axis, comprising a dilator having an axially elongated tubular member that has a proximal end portion and a generally circular outer peripheral surface, and a hub having an axial distal end portion joined to the proximal end portion of the dilator member, a proximal end portion and a locking finger recessed portion, the hub including a main body and a flange that in combination with the main body forms the recessed portion to open radially outwardly relative to the central axis; and an introducer that includes an axially elongated tubular portion for having the dilator member extended thereinto, said tubular portion having a proximal end portion, a tab joined to the proximal end portion of the tubular portion to extend radially outward therefrom for facilitating manual control of the movement of the tubular portion, and a locking finger member proximally mounted on the tab for movement relative to the recessed portion between a first position extending into the recessed portion for blocking any significant, accidental movement of the hub relative to the tab to block axial separation of the tubular member from the tubular portion and a second position exterior of the recessed portion, the locking finger member including a radially extending locking finger for extension into the recessed portion to block axial movement of the hub relative to the tab in a direction away from the hub.

12. The combination of claim 11, further characterized in that the tab is radially elongated and has an end portion remote from the tubular portion, and that the locking finger member includes means for joining the locking finger to the tab in a substantially fixed relationship to the tab radially intermediate the tubular portion and the remote end portion of the tab, the tab being of sufficient flexibility for manual bending to selectively move the locking finger into and out of the recessed portion.

13. The combination of claim 11, further characterized in that the tab is radially elongated and has an end portion radially remote from the tubular portion, that the locking finger member includes means for joining the locking finger to the tab in a substantially fixed relationship to the tab to extend radially toward the central axis, and said hub flange portion including a notch means for angular alignment with the locking finger to permit axial movement of the hub main body relative to the tab, the tubular member and the hub flange portion rotate relative to the tubular portion between a first position that the tubular member is axially extendable into the tubular portion and a second position to block axial separation of the dilator and introducer.

14. An introducer that is usable with a dilator, comprising an axially elongated tubular portion having a central axis of elongation, a distal end portion and a proximal end portion, said tubular portion proximal end portion having a proximal terminal peripheral edge, a radially elongated tab, means for joining the tab to the tubular portion proximal end portion, and a slider means mounted to the tab for radial slidable movement between a position at least substantially out of axial alignment with the terminal peripheral edge for permitting axial movement of the dilator to extend through the terminal peripheral edge and into the proximal end portion, and a valve closed position in abutting relationship to the terminal peripheral edge. For blocking any significant fluid flow through the tubular member.

15. The introducer of claim 14, further characterized in that the tab has opposite sides and radially elongated grooves opening through the tab sides, and that the slider means has a web portion extending proximally of the tab and leg means joined to the web portion and extending into the grooves for mounting the web portion to the tab for axial slidable movement.

16. The introducer of claim 14, further characterized in that the slider means has a radial outer end portion and a radial inner end portion and a locking finger mounted to the radial inner end portion to extend radially inwardly of the slider means.

17. The introducer of claim 16 in combination with the dilation further characterized in that the dilator has an axially elongated tubular member which extends into the tubular portion, the tubular member having a proximal end portion and a distal end portion, and a hub having a distal end portion joined to the tubular member proximal end portion and being abuttable against the tubular portion proximal end portion, and the hub having a radially outwardly extending flange that is extendable axially between the locking finger and the tubular portion proximal end portion when the tubular portion proximal portion is in abutting relationship to the hub distal end portion and when the slider means is in a position radially outwardly of the slider means in the valve closed position.

18. The combination of claim 17, further characterized in that the tab has radially elongated grooves and that the slider means has inturned means extending into the grooves for mountingly retaining the slider means on the tab for slidable movement radially outward to a position that the locking finger is out of axial alignment with the flange when the tubular portion proximal end portion is in abutting relationship to the hub distal end portion.

* * * * *